(12) United States Patent
Sakamoto et al.

(10) Patent No.: US 9,150,677 B2
(45) Date of Patent: Oct. 6, 2015

(54) POLYMERIZABLE COMPOUNDS, POLYMERIZABLE COMPOSITION, POLYMER, AND OPTICALLY ANISOTROPIC BODY

(75) Inventors: Kei Sakamoto, Tokyo (JP); Kumi Okuyama, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 92 days.

(21) Appl. No.: 14/129,055

(22) PCT Filed: Jun. 14, 2012

(86) PCT No.: PCT/JP2012/065202
§ 371 (c)(1),
(2), (4) Date: Jan. 22, 2014

(87) PCT Pub. No.: WO2012/176679
PCT Pub. Date: Dec. 27, 2012

(65) Prior Publication Data
US 2014/0309396 A1    Oct. 16, 2014

(30) Foreign Application Priority Data

Jun. 24, 2011  (JP) ................. 2011-140097

(51) Int. Cl.
| C08F 122/10 | (2006.01) |
| C07C 251/88 | (2006.01) |
| C08F 222/10 | (2006.01) |
| G02B 5/30 | (2006.01) |

(52) U.S. Cl.
CPC ............. *C08F 122/10* (2013.01); *C07C 251/88* (2013.01); *C08F 222/1006* (2013.01); *G02B 5/3016* (2013.01)

(58) Field of Classification Search
CPC ................. C07C 251/88; C08F 122/10; C08F 222/1006; G02B 5/3016
USPC ..................... 526/310, 312; 560/61
See application file for complete search history.

(56) References Cited

U.S. PATENT DOCUMENTS

| 5,567,349 | A | 10/1996 | Kelly et al. |
| 6,139,771 | A | 10/2000 | Walba et al. |
| 6,203,724 | B1 | 3/2001 | Reiffenrath et al. |
| 6,565,974 | B1 | 5/2003 | Uchiyama et al. |
| 2002/0159005 | A1 | 10/2002 | Arakawa et al. |
| 2003/0102458 | A1 | 6/2003 | Nishikawa et al. |
| 2007/0176145 | A1 | 8/2007 | Nishikawa et al. |
| 2007/0298191 | A1 | 12/2007 | Yamahara et al. |
| 2009/0072194 | A1 | 3/2009 | Yamahara et al. |
| 2009/0189120 | A1 | 7/2009 | Takeuchi |
| 2010/0201920 | A1 | 8/2010 | Adlem et al. |
| 2010/0258764 | A1 | 10/2010 | Sakamoto et al. |
| 2010/0301271 | A1 | 12/2010 | Adlem et al. |
| 2014/0200320 | A1* | 7/2014 | Sakamoto et al. ............ 526/312 |

FOREIGN PATENT DOCUMENTS

| JP | 10-68816 A | 3/1998 |
| JP | 10-90521 A | 4/1998 |
| JP | 11-52131 A | 2/1999 |
| JP | 2001-4837 A | 1/2001 |
| JP | 2002-267838 A | 9/2002 |
| JP | 2005-208414 A | 8/2005 |
| JP | 2005-208415 A | 8/2005 |
| JP | 2005-208416 A | 8/2005 |
| JP | 2005-289980 A | 10/2005 |
| JP | 2008-291218 A | 12/2008 |
| JP | 2010-31223 A | 2/2010 |

(Continued)

OTHER PUBLICATIONS

International Search Report issued in PCT/JP2012/065202, dated Sep. 4, 2012.

*Primary Examiner* — Ling Choi
*Assistant Examiner* — Chun-Cheng Wang
(74) *Attorney, Agent, or Firm* — Birch, Stewart, Kolasch & Birch, LLP

(57) ABSTRACT

The invention is a polymerizable compound represented by formula (I); a polymerizable composition comprising the polymerizable compound and an initiator; a polymer obtained by polymerizing the polymerizable compound or the polymerizable composition, and an optically anisotropic article comprising the polymer. In the formula, $Q^1$ to $Q^3$ are a hydrogen atom, and the like; X is a C4-12 divalent aromatic group, and the like; $Y^1$ to $Y^{12}$ are a chemical single bond, —O—, —O—C(=O)—, —C(=O)—O—, and the like; $G^1$ to $G^4$ are a C1-20 divalent aliphatic group, and the like; $Z^1$ to $Z^4$ are a C2-10 alkenyl group, and the like; $A^1$ is a trivalent aromatic group, and the like; $A^2$ to $A^7$ are a C4-30 divalent aromatic group, and the like; and n is 0 or 1. The present invention provides a polymerizable compound, a polymerizable composition, and a polymer that have a practical low melting point, exhibit excellent solubility in a general-purpose solvent, can be produced at low cost, and may produce an optical film that achieves uniform conversion of polarized light over a wide wavelength band, and an optically anisotropic article.

$$Z^1-Y^5-G^1-Y^3-A^2-Y^1-A^1-Y^2-A^3-Y^4-G^2-Y^6-Z^2 \quad (I)$$

(with branch: $A^4-Y^7-A^5-Y^8-G^3-Y^9-Z^3$ and $A^6-Y^{10}-A^7-Y^{11}-G^4-Y^{12}-Z^4$, subscript $n$)

20 Claims, No Drawings

(56) References Cited

FOREIGN PATENT DOCUMENTS

| JP | 2010-537954 A | 12/2010 |
| JP | 2011-6360 A | 1/2011 |
| JP | 2011-6361 A | 1/2011 |
| JP | 2011-42606 A | 3/2011 |
| WO | WO00/26705 A1 | 5/2000 |

* cited by examiner

POLYMERIZABLE COMPOUNDS, POLYMERIZABLE COMPOSITION, POLYMER, AND OPTICALLY ANISOTROPIC BODY

TECHNICAL FIELD

The invention relates to a polymerizable compound, a polymerizable composition, and a polymer that may produce an optical film that achieves uniform conversion of polarized light over a wide wavelength band, and also relates to an optically anisotropic article.

A flat panel display (FPD) that utilizes an optical film (e.g., polarizer and retardation film) can achieve high-resolution display, and has been widely used as a display device (e.g., TV) that achieves high performance.

Examples of the retardation film include a quarter-wave plate that converts linearly polarized light into circularly polarized light, and a half-wave plate that converts the plane of vibration of linearly polarized light by 90°. Such a retardation film can achieve accurate conversion of specific monochromatic light so that ¼λ or ½λ retardation occurs.

However, a known retardation film has a problem in that polarized light that passes through the retardation film is converted into colored polarized light. Specifically, since a material that forms the retardation film has wavelength dispersion with regard to retardation, and a polarization state distribution corresponding to each wavelength occurs for white light that includes different light beams in the visible region, it is impossible to achieve accurate ¼λ, or ½λ retardation over the entire wavelength band.

In order to solve the above problem, various wideband retardation films that can achieve uniform retardation for light over a wide wavelength band (i.e., retardation films having reverse wavelength dispersion) have been studied (see Patent Documents 1 to 6, for example).

It has been desired to reduce the thickness of the flat panel display as much as possible along with an improvement in performance and widespread use of mobile information terminals (e.g., mobile personal computer and mobile phone). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been proposed (see Patent Documents 7 to 24, for example).

However, the low-molecular-weight polymerizable compounds or the polymerizable compositions disclosed in Patent Documents 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, and low solubility in a solvent generally used for an industrial process, or the temperature range in which liquid crystallinity is obtained may be very narrow. Moreover, since the above low-molecular-weight polymerizable compounds and the like are synthesized in a plurality of steps using a synthesis method that utilizes an expensive reagent, the production cost increases.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2011-6360
Patent Document 17: JP-A-2011-6361
Patent Document 18: JP-A-2011-42606
Patent Document 19: JP-T-2010-537954 (US20100201920A1)
Patent Document 20: JP-T-2010-537955 (US20100301271A1)
Patent Document 21: WO2006/052001 (US20070298191A1)
Patent Document 22: U.S. Pat. No. 6,139,771
Patent Document 23: U.S. Pat. No. 6,203,724
Patent Document 24: U.S. Pat. No. 5,567,349

SUMMARY OF THE INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, can be produced at low cost, and may produce an optical film that achieves uniform conversion of polarized light over a wide wavelength band, and an optically anisotropic article.

Solution to Problem

The inventors of the invention conducted extensive studies in order to achieve the above object. As a result, the inventors found that an optical film that achieves uniform conversion of polarized light over a wide wavelength band, and shows satisfactory performance can be inexpensively produced by utilizing a polymerizable compound represented by the following general formula (I), a polymerizable composition that includes the polymerizable compound and an initiator, a polymer obtained by polymerizing the polymerizable compound or the polymerizable composition, and an optically anisotropic article that includes the polymer. This finding has led to the completion of the invention.

Several aspects of the invention provide the following polymerizable compound (see (1) to (7)), polymerizable composition (see (8)), polymer (see (9)), and optically anisotropic body (see (10)).

(1) A polymerizable compound represented by the following general formula (I),

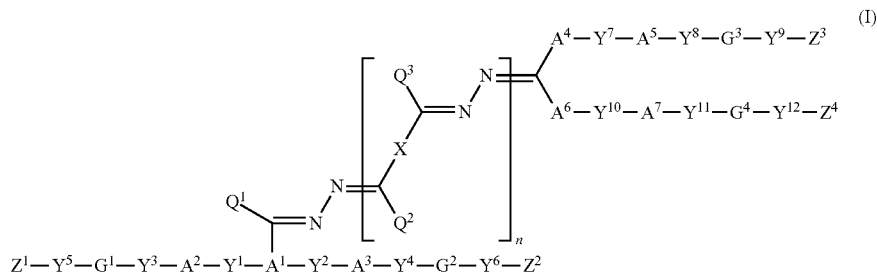

wherein $Q^1$ to $Q^3$ are independently a hydrogen atom, or a substituted or unsubstituted alkyl group having 1 to 6 carbon atoms,
X is a substituted or unsubstituted divalent aromatic group having 4 to 12 carbon atoms, $Y^1$ to $Y^{12}$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms,
$G^1$ to $G^4$ are independently a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)— (excluding a case where the aliphatic group includes two or more adjacent —O— or —S—), $R^2$ is a hydrogen atom or an alkyl group having 1 to 6 carbon atoms,
$Z^1$ to $Z^4$ are independently an alkenyl group having 2 to 10 carbon atoms that is substituted with a halogen atom, or unsubstituted,
$A^1$ is a substituted or unsubstituted trivalent aromatic group,
$A^2$ to $A^7$ are independently a substituted or unsubstituted divalent aromatic group having 4 to 30 carbon atoms, and n is 0 or 1.
(2) The polymerizable compound according to (1), wherein $A^1$ in the general formula (I) is a substituted or unsubstituted trivalent benzene ring group, or a substituted or unsubstituted trivalent naphthalene ring group, and $A^2$ to $A^7$ in the general formula (I) are independently a substituted or unsubstituted phenylene group, or a substituted or unsubstituted naphthylene group.
(3) The polymerizable compound according to (1) or (2), wherein $Y^1$ to $Y^{12}$ in the general formula (I) are independently a chemical single bond, —O—, —O—C(=O)—, —C(=O)—O—, or —O—C(=O)—O—.
(4) The polymerizable compound according to any one of (1) to (3), wherein $Z^1$ to $Z^4$ in the general formula (I) are independently $CH_2$=CH—, $CH_2$=C(CH$_3$)—, or $CH_2$=C(Cl)—.
(5) The polymerizable compound according to any one of (1) to (4), wherein $G^1$ to $G^4$ in the general formula (I) are independently a substituted or unsubstituted divalent aliphatic group having 1 to 12 carbon atoms that optionally includes —O—, —O—C(=O)—, —C(=O)—O—, or —C(=O)— (excluding a case where the aliphatic group includes two or more adjacent —O—).
(6) The polymerizable compound according to any one of (1) to (5), wherein X in the general formula (I) is a substituted or unsubstituted phenylene group, a substituted or unsubstituted naphthylene group, or a substituted or unsubstituted biphenylene group.
(7) The polymerizable compound according to any one of (1) to (6), wherein $A^1$ in the general formula (I) is a substituted or unsubstituted trivalent benzene ring group, $A^2$ to $A^7$ in the general formula (I) are independently a substituted or unsubstituted phenylene group, $Y^1$ to $Y^{12}$ in the general formula (I) are independently a chemical single bond, —O—, —O—C(=O)—, —C(=O)—O—, or —O—C(=O)—O—, $Z^1$ to $Z^4$ in the general formula (I) are independently $CH_2$=CH—, $CH_2$=C(CH$_3$)—, or $CH_2$=C(Cl)—, and $G^1$ to $G^4$ in the general formula (I) are independently a divalent alkylene group having 1 to 12 carbon atoms.
(8) A polymerizable composition including at least one type of the polymerizable compound according to any one of (1) to (7), and an initiator.
(9) A polymer obtained by polymerizing the polymerizable compound according to any one of (1) to (7), or the polymerizable composition according to (8).
(10) An optically anisotropic article including the polymer according to (9).

Advantageous Effects of the Invention

The polymerizable compound, the polymerizable composition, and the polymer according to the aspects of the invention make it possible to inexpensively obtain an optical film that achieves uniform conversion of polarized light over a wide wavelength band, and shows satisfactory performance.

Since the optically anisotropic article according to one aspect of the invention is produced using the polymer according to one aspect of the invention, it is possible to easily form an optical film that can be obtained at low cost, achieves uniform conversion of polarized light over a wide wavelength band, and shows satisfactory performance. For example, an antireflective film may be produced by combining the optically anisotropic article with a polarizer, and may suitably be used to prevent reflection from a touch panel, an organic electroluminescent device, and the like.

A polymerizable compound, a polymerizable composition, a polymer, and an optically anisotropic article according to exemplary embodiments of the invention are described in detail below.
1) Polymerizable Compound
A polymerizable compound according to one embodiment of the invention is a compound represented by the general formula (I).

$Q^1$ to $Q^3$ in the general formula (I) are independently a hydrogen atom, or a substituted or unsubstituted alkyl group having 1 to 6 carbon atoms.

Examples of the (unsubstituted) alkyl group having 1 to 6 carbon atoms include a methyl group, an ethyl group, an n-propyl group, an isopropyl group, an n-butyl group, a sec-butyl group, a t-butyl group, an n-pentyl group, an n-hexyl group, and the like.

Examples of a substituent that may substitute the alkyl group having 1 to 6 carbon atoms include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

It is preferable that $Q^1$ to $Q^3$ be independently a hydrogen atom or an alkyl group having 1 to 6 carbon atoms, and more preferably a hydrogen atom or a methyl group.

X in the general formula (I) is a substituted or unsubstituted divalent aromatic group having 4 to 12 carbon atoms.

The aromatic group represented by X may be a monocyclic aromatic group, a polycyclic aromatic group, or an aromatic group in which a plurality of aromatic rings are bonded.

Examples of the aromatic group represented by X are shown below. Note that "-" in the following formulas indicates a chemical bond (hereinafter the same).

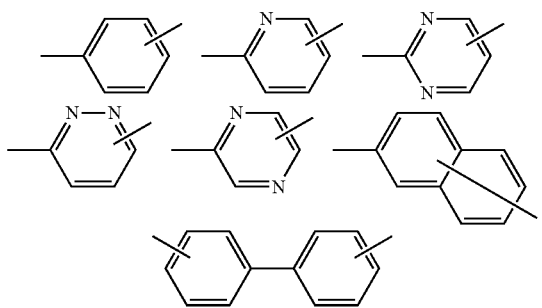

These aromatic groups may be substituted with a substituent at an arbitrary position. Examples of the substituent include halogen atoms, a cyano group, a hydroxyl group, alkyl groups having 1 to 6 carbon atoms, alkoxy groups having 1 to 6 carbon atoms, a nitro group, a —C(=O)—OR$^a$ group (wherein R$^a$ is an alkyl group having 1 to 6 carbon atoms), and the like. Among these, halogen atoms, alkyl groups having 1 to 6 carbon atoms, and alkoxy groups having 1 to 6 carbon atoms are preferable, and a fluorine atom, alkyl groups having 1 to 3 carbon atoms such as a methyl group, an ethyl group, and a propyl group, and alkoxy groups having 1 to 3 carbon atoms such as a methoxy group, an ethoxy group, and a propoxy group are more preferable.

The aromatic group represented by X is preferably a substituted or unsubstituted phenylene group, a substituted or unsubstituted naphthylene group, or a substituted or unsubstituted biphenylene group, more preferably a substituted or unsubstituted phenylene group or a substituted or unsubstituted naphthylene group, still more preferably the group represented by the following formula (X1) or the group represented by the following formula (X2), and particularly preferably the group represented by the following formula (X1), in order to ensure that the intended effects of the invention can be more advantageously achieved.

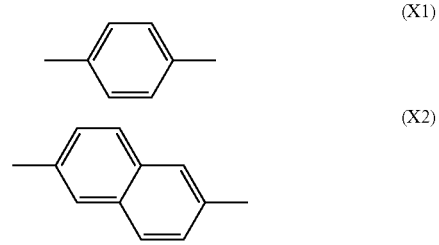

$Y^1$ to $Y^{12}$ in the general formula (I) are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^{12}$ be independently a chemical single bond, —O—, —O—C(=O)—, —C(=O)—O—, or —O—C(=O)—O—.

$G^1$ to $G^4$ in the general formula (I) are independently a substituted or unsubstituted divalent aliphatic group having 1 to 20 carbon atoms.

Examples of the divalent aliphatic group having 1 to 20 carbon atoms include aliphatic groups having a linear structure; aliphatic groups having an alicyclic structure such as a saturated cyclic hydrocarbon (cycloalkane) structure or an unsaturated cyclic hydrocarbon (cycloolefin) structure; and the like.

Examples of a substituent that may substitute the divalent aliphatic group having 1 to 20 carbon atoms include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)— (provided that a case where the aliphatic group includes two or more adjacent —O— or —S— is excluded).

Among these, —O—, —O—C(=O)—, —C(=O)—O—, and —C(=O)— are preferable.

$R^2$ is a hydrogen atom or an alkyl group having 1 to 6 carbon atoms similar to that represented by $R^1$, and is preferably a hydrogen atom or a methyl group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, —CH$_2$—C(=O)—CH$_2$—, and the like.

It is preferable that $G^1$ to $G^4$ be independently a substituted or unsubstituted divalent aliphatic group having 1 to 12 carbon atoms that optionally includes —O—, —O—C(=O)—, —C(=O)—O—, or —C(=O)— (excluding a case where the aliphatic group includes two or more adjacent —O—), more preferably an aliphatic group having a linear structure (e.g., alkylene group having 1 to 20 carbon atoms or alkenylene group having 2 to 20 carbon atom), more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—(CH$_2$)$_4$—) or a hexamethylene group (—(CH$_2$)$_6$—), in order to ensure that the intended effects of the invention can be more advantageously achieved.

$Z^1$ to $Z^4$ in the general formula (I) are independently an alkenyl group having 2 to 10 carbon atoms that is substituted with a halogen atom, or unsubstituted.

The number of carbon atoms of the alkenyl group is preferably 2 to 6. Examples of the halogen atom that may substitute the alkenyl group represented by $Z^1$ to $Z^4$ include a fluorine atom, a chlorine atom, a bromine atom, and the like. Among these, a chlorine atom is preferable.

Specific examples of the alkenyl group having 2 to 10 carbon atoms represented by $Z^1$ to $Z^4$ that is substituted with a halogen atom, or unsubstituted, include CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$C=CH—CH$_2$—CH$_2$—, CH$_2$=C(Cl)—, CH$_2$=C(CH$_3$)—CH$_2$—, CH$_3$—CH=CH—CH$_2$—, and the like.

It is preferable that $Z^1$ to $Z^4$ be independently CH$_2$=CH—, CH$_2$=C(CH$_3$)—, CH$_2$=C(Cl)—, CH$_2$=CH—CH$_2$—, CH$_2$=C(CH$_3$)—CH$_2$—, or CH$_2$=C(CH$_3$)—CH$_2$—CH$_2$—, more preferably CH$_2$=CH—, CH$_2$=C(CH$_3$)—, or CH$_2$=C(Cl)—, and still more preferably CH$_2$=CH—, in order to ensure that the intended effects of the invention can be more advantageously achieved.

$A^1$ in the general formula (I) is a substituted or unsubstituted trivalent aromatic group. The trivalent aromatic group may be a trivalent carbocyclic aromatic group, or may be a trivalent heterocyclic aromatic group. It is preferable that the trivalent aromatic group be a trivalent carbocyclic aromatic group, and more preferably a trivalent benzene ring group or a trivalent naphthalene ring group represented by the following formulas. Note that the substituents $Y^1$ and $Y^2$ are also shown in the following formulas so that the bonding state can be easily understood ($Y^1$ and $Y^2$ are the same as defined above; hereinafter the same).

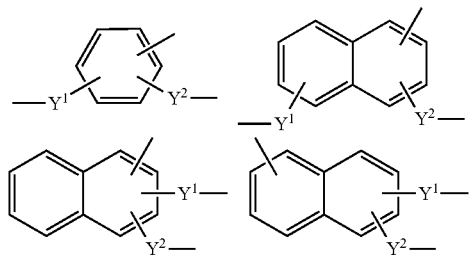

$A^1$ is more preferably any of the groups represented by the following formulas (A11) to (A18), and particularly preferably the group represented by the formula (A11).

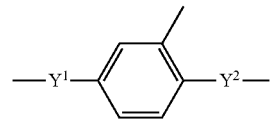 (A11)

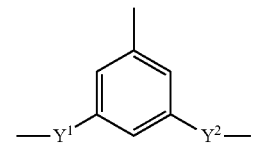 (A12)

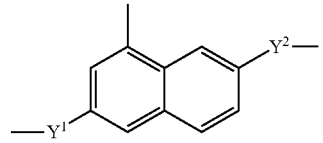 (A13)

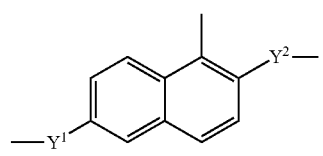 (A14)

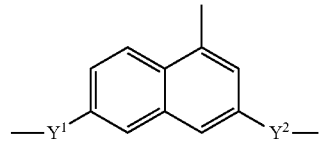 (A15)

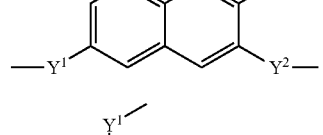 (A16)

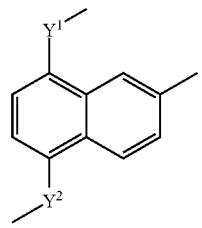 (A17)

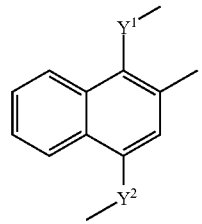 (A18)

The trivalent aromatic group represented by $A^1$ is preferably unsubstituted, but may be substituted with a substituent. Examples of the substituent include halogen atoms such as a fluorine atom and a chlorine atom; a cyano group; alkyl groups having 1 to 6 carbon atoms such as a methyl group, an ethyl group, and a propyl group; alkenyl groups having 2 to 6 carbon atoms such as a vinyl group and an allyl group; alkyl halide groups having 1 to 6 carbon atoms such as a trifluoromethyl group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; a —C(=O)—OR$^b$ group; an —SO$_2$R$^b$ group; and the like. Note that R$^b$ is an alkyl group having 1 to 6 carbon atoms or an aryl group having 6 to 14 carbon atoms.

A$^2$ to A$^7$ in the general formula (I) are independently a substituted or unsubstituted divalent aromatic group having 4 to 30 carbon atoms.

The aromatic group represented by A$^2$ to A$^7$ may be a monocyclic aromatic group, or may be a polycyclic aromatic group.

Specific examples of the aromatic group represented by A$^2$ to A$^7$ are shown below.

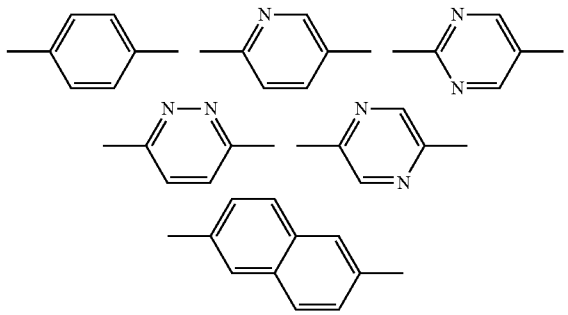

Examples of a substituent that may substitute the aromatic group include halogen atoms, a cyano group, a hydroxyl group, alkyl groups having 1 to 6 carbon atoms, alkoxy groups having 1 to 6 carbon atoms, a nitro group, a —C(=O)—OR$^c$ group, and the like. Note that R$^c$ is an alkyl group having 1 to 6 carbon atoms. Among these, halogen atoms, alkyl groups having 1 to 6 carbon atoms, and alkoxy groups having 1 to 6 carbon atoms are preferable, and a fluorine atom, alkyl groups having 1 to 3 carbon atoms such as a methyl group, an ethyl group, and a propyl group, and alkoxy groups having 1 to 3 carbon atoms such as a methoxy group, an ethoxy group, and a propoxy group are more preferable.

It is preferable that A$^2$ to A$^7$ be independently a substituted or unsubstituted phenylene group or a substituted or unsubstituted naphthylene group, more preferably the group represented by the following formula (A21) or (A22), and particularly preferably the group represented by the formula (A21), in order to ensure that the intended effects of the invention can be more advantageously achieved.

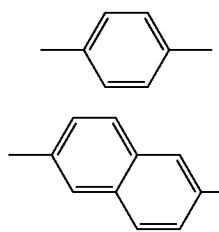

(A21)

(A22)

n in the general formula (I) is 0 or 1, and preferably 0.

In order to ensure that the intended effects of the invention can be more advantageously achieved, it is preferable that the polymerizable compound represented by the general formula (I) be:

(i) the polymerizable compound represented by the general formula (I) wherein A$^1$ in the general formula (I) is a substituted or unsubstituted trivalent benzene ring group, A$^2$ to A$^7$ in the general formula (I) are independently a substituted or unsubstituted phenylene group, Y$^1$ to Y$^{12}$ in the general formula (I) are independently a chemical single bond, —O—, —O—C(=O)—, —C(=O)—O—, or —O—C(=O)—O—, Z$^1$ to Z$^4$ in the general formula (I) are independently CH$_2$=CH—, CH$_2$=C(CH$_3$)—, or CH$_2$=C(Cl)—, and G$^1$ to G$^4$ in the general formula (I) are independently a divalent alkylene group having 1 to 12 carbon atoms, (ii) more preferably the polymerizable compound represented by the general formula (I) wherein n in the general formula (I) is 0, A$^1$ in the general formula (I) is a substituted or unsubstituted trivalent benzene ring group, A$^2$ to A$^7$ in the general formula (I) are independently a substituted or unsubstituted phenylene group, Y$^1$ to Y$^{12}$ in the general formula (I) are independently a chemical single bond, —O—, —O—C(=O)—, —C(=O)—O—, or —O—C(=O)—O—, Z$^1$ to Z$^4$ in the general formula (I) are independently CH$_2$=CH—, CH$_2$=C(CH$_3$)—, or CH$_2$=C(Cl)—, and G$^1$ to G$^4$ in the general formula (I) are independently a divalent alkylene group having 1 to 12 carbon atoms, and (iii) particularly preferably the polymerizable compound represented by the general formula (I) wherein n in the general formula (I) is 0, A$^1$ in the general formula (I) is a substituted or unsubstituted trivalent benzene ring group, A$^2$ to A$^7$ in the general formula (I) are independently a substituted or unsubstituted phenylene group, Y$^1$ to Y$^{12}$ in the general formula (I) are independently a chemical single bond, —O—, —O—C(=O)—, —C(=O)—O—, or —O—C(=O)—O—, Z$^1$ to Z$^4$ in the general formula (I) are independently CH$_2$=CH—, CH$_2$=C(CH$_3$)—, or CH$_2$=C(Cl)—, G$^1$ to G$^4$ in the general formula (I) are independently a divalent alkylene group having 1 to 12 carbon atoms, and the group represented by Z$^2$—Y$^6$-G$^2$-Y$^4$-A$^3$-Y$^2$ is identical with the group represented by Z$^1$—Y$^5$-G$^1$-Y$^3$-A$^2$-Y$^1$, and/or the group represented by Z$^3$—Y$^9$-G$^3$-Y$^8$-A$^5$-Y$^7$— is identical with the group represented by Z$^4$—Y$^{12}$-G$^4$-Y$^{11}$-A$^7$-Y$^{10}$—.

Note that the polymerizable compound represented by the general formula (I) may be a stereoisomer based on the carbon-nitrogen double bond. These stereoisomers are also intended to be included within the scope of the invention.

The polymerizable compound according to one embodiment of the invention may typically be produced by appropriately bonding and modifying a plurality of known compounds having a desired structure by arbitrarily combining a carbon-nitrogen double bond (—C=N—)-forming reaction, an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

Specific examples of a method for producing the polymerizable compound according to one embodiment of the invention are described below.

The following description is given taking an example in which Y$^7$, Y$^{10}$, Y$^1$, and Y$^2$ in the general formula (I) are respectively a group represented by Y$^{7'}$—C(=O)—O—, a group represented by Y$^{10'}$—C(=O)—O—, a group represented by Y$^{1'}$—C(=O)—O—, and a group represented by Y$^{2'}$—C(=O)—O—. Note that the polymerizable compound according to one embodiment of the invention is not limited thereto.

Production Method 1

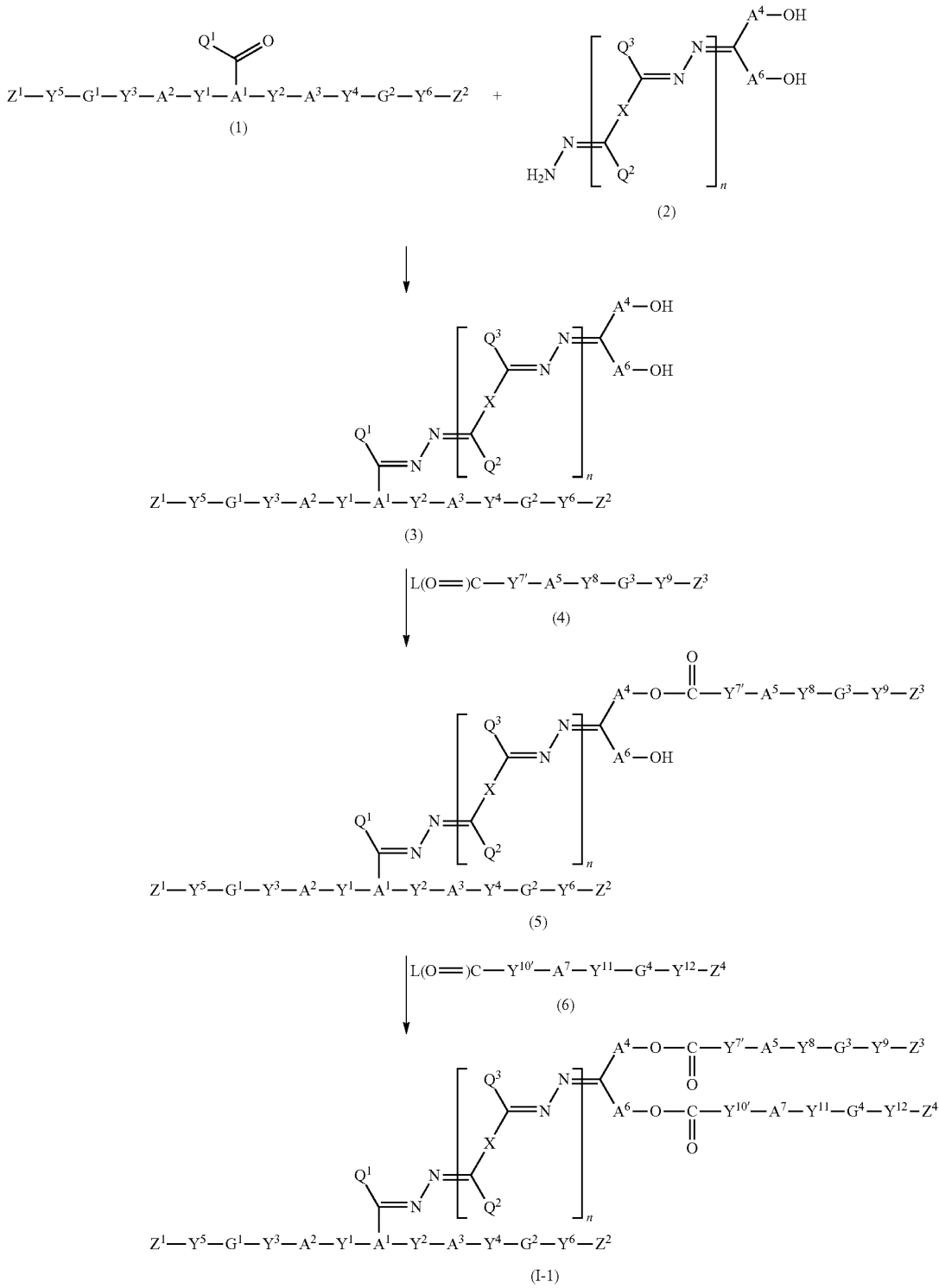

wherein $A^1$ to $A^7$, $Q^1$ to $Q^3$, X, $Y^1$ to $Y^6$, $Y^8$, $Y^9$, $Y^{11}$, $Y^{12}$, $G^1$ to $G^4$, $Z^1$ to $Z^4$, and n are the same as defined above, the group represented by $Y^{7'}$—C(=O)—O— is one type of $Y^7$, the group represented by $Y^{10'}$—C(=O)—O— is one type of $Y^{10}$, and L is a leaving group (e.g., hydroxyl group, halogen atom, methanesulfonyloxy group, or p-toluenesulfonyloxy group).

The production method 1 is a method that produces the polymerizable compound represented by the general formula (I-1) (polymerizable compound (I-1)) wherein $Y^7$ in the general formula (I) is the group represented by $Y^{7'}$—C(=O)—O—, and $Y^{10}$ in the general formula (I) is the group represented by $Y^{10'}$—C(=O)—O—.

Specifically, the compound represented by the formula (2) (compound (2)) is reacted with the carbonyl compound represented by the formula (1) (carbonyl compound (1)) in an appropriate solvent in a molar ratio (carbonyl compound (1): compound (2)) of 1:1 to 1:2 (preferably 1:1 to 1:1.5) to obtain the compound represented by the formula (3) (compound (3)) (step 1), and the compound (3) is isolated, and reacted with the compound represented by the formula (4) (compound (4)) in an appropriate solvent in a molar ratio (compound (3): compound (4)) of 1:1 to 1:1.2 to obtain the compound represented by the formula (5) (compound (5)) (step 2).

The compound (5) is isolated, and reacted with the compound represented by the formula (6) (compound (6)) in an appropriate solvent in a molar ratio (compound (5):compound (6)) of 1:1 to 1:1.5 to obtain the target polymerizable compound (I-1) (step 3).

The subsequent reaction may be effected using the crude product after the step 1 and/or the step 2 without performing the isolation operation, and the target compound may be isolated from the resulting reaction mixture.

Step 1

The solvent used in the step 1 is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; ether-based solvents such as diethyl ether, tetrahydrofuran, 1,2-dimethoxyethane, 1,4-dioxane, and cyclopentyl methyl ether; ester-based solvents such as ethyl acetate, propyl acetate, and methyl propionate; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents including two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of the compounds used for the reaction in total.

Examples of a dehydrating agent include an acidic catalyst such as hydrochloric acid, sulfuric acid, phosphoric acid, potassium hydrogen sulfate, oxalic acid, p-toluenesulfonic acid, (±)-10-camphorsulfonic acid, and a boron trifluoride ether complex; a basic catalyst such as sodium hydroxide and potassium hydroxide; and the like.

The dehydrating agent is normally used in an amount of 0.05 to 5 mol based on 1 mol of the carbonyl compound (1).

The reaction proceeds smoothly when the reaction temperature is within the range from −10° C. to the boiling point of the solvent. The reaction time is determined taking account of the reaction scale, but is normally several minutes to several tens of hours.

Step 2

When the compound (4) is a compound (carboxylic acid) represented by the formula (4) wherein L is a hydroxyl group, the target product can be obtained by effecting the reaction between the compound (3) and the compound (4) in the presence of a dehydration-condensation agent (e.g., 1-ethyl-3-(3-dimethylaminopropyl)carbodiimide hydrochloride (WSC) or dicyclohexylcarbodiimide).

The dehydration-condensation agent is normally used in an amount of 1 to 3 mol based on 1 mol of the compound (4).

When the compound (4) is a compound (acid halide) represented by the formula (4) wherein L is a halogen atom, the target product can be obtained by effecting the reaction in the presence of a base.

Examples of the base include organic bases such as triethylamine, pyridine, and 4-(dimethylamino)pyridine, and inorganic bases such as sodium hydroxide, sodium carbonate, and sodium hydrogen carbonate.

The base is normally used in an amount of 1 to 3 mol based on 1 mol of the compound (4).

When the compound (4) is a compound (mixed acid anhydride) represented by the formula (4) wherein L is a methanesulfonyloxy group or a p-toluenesulfonyloxy group, the target product can be obtained in the same manner as in the case where L is a halogen atom.

Examples of the solvent used for the above reaction include chlorine-based solvents such as chloroform and methylene chloride; amide-based solvents such as N-methylpyrrolidone, N,N-dimethylformamide, N,N-dimethylacetamide, and hexamethylphosphoric triamide; ether-based solvents such as 1,4-dioxane, cyclopentyl methyl ether, tetrahydrofuran, and tetrahydropyran; sulfur-containing solvents such as dimethyl sulfoxide and sulfolane; aromatic hydrocarbon-based solvents such as benzene, toluene, and xylene; aliphatic hydrocarbon-based solvents such as n-pentane, n-hexane, and n-octane; alicyclic hydrocarbon-based solvents such as cyclopentane and cyclohexane; mixed solvents including two or more solvents among these solvents; and the like.

The solvent may be used in an appropriate amount taking account of the type of each compound, the reaction scale, and the like. The solvent is normally used in an amount of 1 to 100 g per gram of the compound (3).

The reaction proceeds smoothly when the reaction temperature is within the range from −10° C. to the boiling point of the solvent. The reaction time is determined taking account of the reaction scale, but is normally several minutes to several tens of hours.

Step 3

The step 3 in which the compound (6) is reacted with the resulting compound (5) may be implemented in the same manner as the step 2.

When producing a polymerizable compound (I-2) wherein the group represented by $Z^3$—$Y^9$-$G^3$-$Y^8$-$A^5$-$Y^{7'}$— is identical with the group represented by $Z^4$—$Y^{12}$-$G^4$-$Y^{11}$-$A^7$-$Y^{10'}$—, the compound (3) may be reacted with a 2-fold equivalent of the compound (4) in the step 2 (see the following reaction formula) to produce the target polymerizable compound (I-2) in one step.

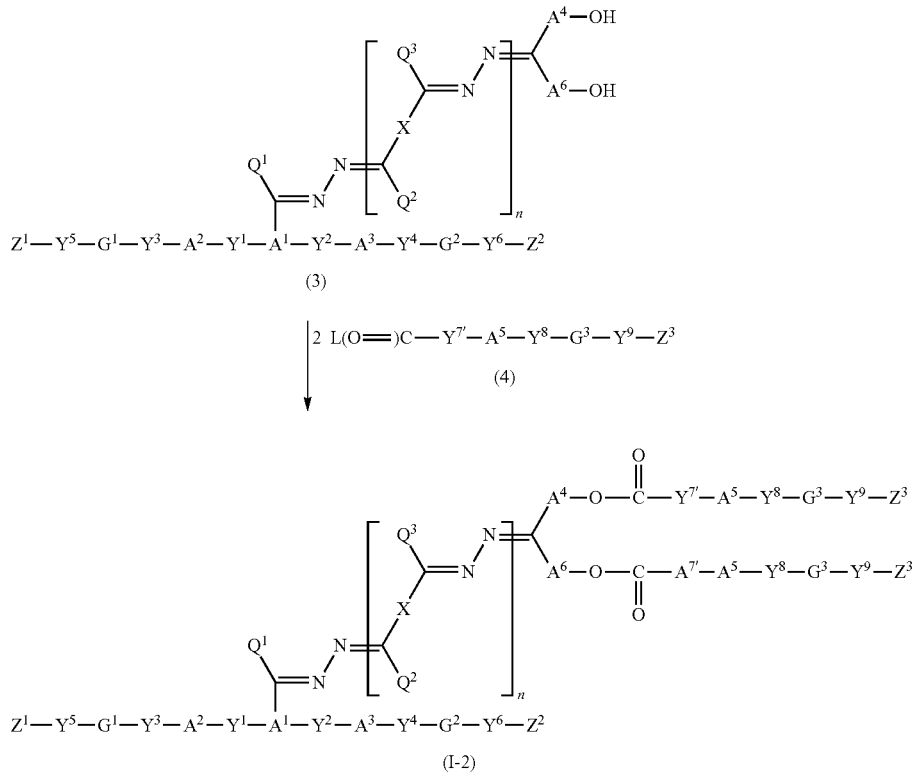
Production Method 2
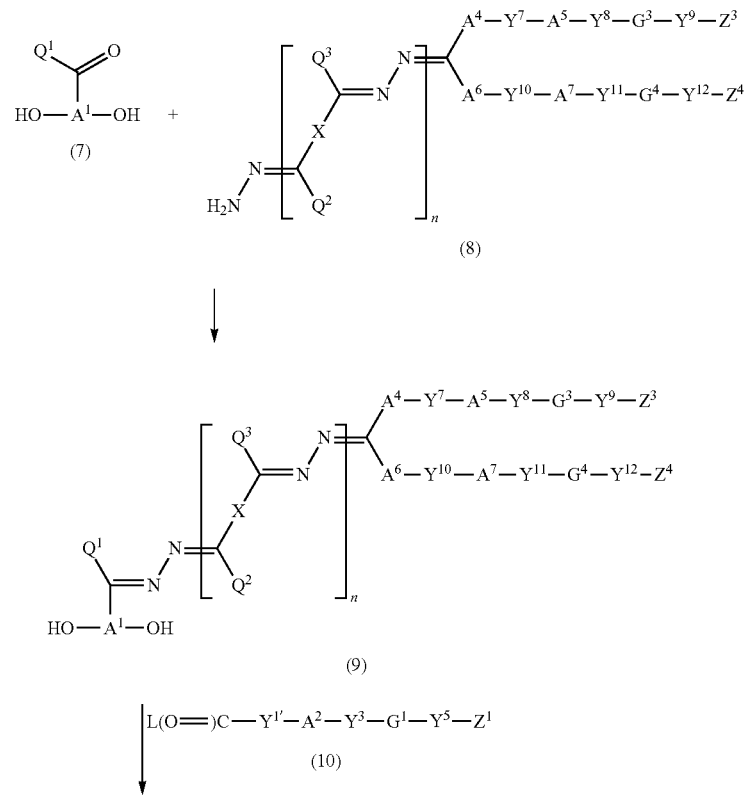

-continued

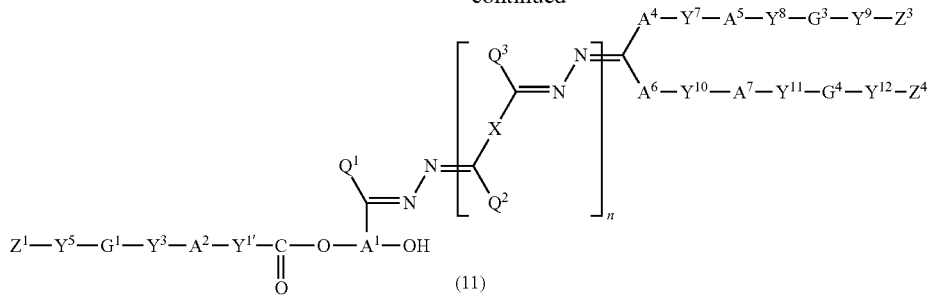

(11)

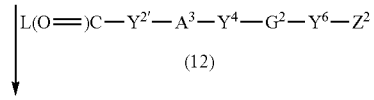

(12)

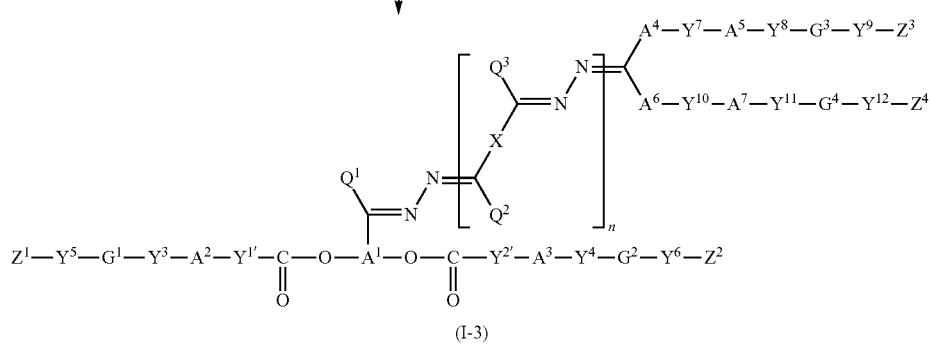

(I-3)

wherein $A^1$ to $A^7$, $Q^1$ to $Q^3$, X, $Y^3$ to $Y^{12}$, $G^1$ to $G^4$, $Z^1$ to $Z^4$, n, and L are the same as defined above, the group represented by $Y^{1'}$—C(=O)—O— is one type of $Y^1$, and the group represented by $Y^{2'}$—C(=O)—O— is one type of $Y^2$.

The production method 2 is a method that produces the polymerizable compound represented by the general formula (I-3) (polymerizable compound (I-3)) wherein $Y^1$ in the general formula (I) is the group represented by $Y^{1'}$—C(=O)—O—, and $Y^2$ in the general formula (I) is the group represented by $Y^{2'}$—C(=O)—O—.

Specifically, the compound represented by the formula (8) (compound (8)) is reacted with the carbonyl compound represented by the formula (7) (carbonyl compound (7)) in an appropriate solvent in a molar ratio (carbonyl compound (7): compound (8)) of 1:1 to 2:1 (preferably 1:1 to 1.5:1) to obtain the compound represented by the formula (9) (compound (9)) (step 1), and the compound (9) is isolated, and reacted with the compound represented by the formula (10) (compound (10)) in an appropriate solvent in a molar ratio (compound (9):compound (10)) of 1:1 to 1:1.2 to obtain the compound represented by the formula (11) (compound (11)) (step 2).

The compound (11) is isolated, and reacted with the compound represented by the formula (12) (compound (12)) in an appropriate solvent in a molar ratio (compound (11):compound (12)) of 1:1 to 1:1.5 to obtain the target polymerizable compound (I-3) (step 3).

The subsequent reaction may be effected after the step 1 and/or the step 2 without performing the isolation operation, and the target compound may be isolated from the resulting reaction mixture.

The step 1 of the production method 2 may be implemented in the same manner as the step 1 of the production method 1, and the steps 2 and 3 of the production method 2 may be implemented in the same manner as the steps 2 and 3 of the production method 1.

When producing a polymerizable compound (I-4) wherein the group represented by $Z^1$—$Y^5$-$G^1$-$Y^3$-$A^2$-$Y^{1'}$— is identical with the group represented by $Z^2$—$Y^6$-$G^2$-$Y^4$-$A^3$-$Y^{2'}$—, the compound (9) may be reacted with a 2-fold equivalent of the compound (10) in the step 2 (see the following reaction formula) to produce the target polymerizable compound (I-4) in one step.

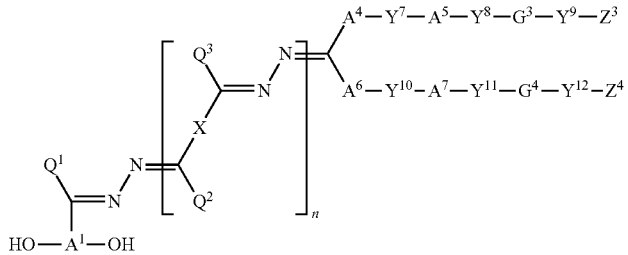

(9)

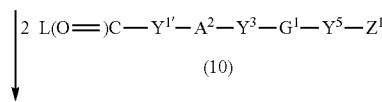

(10)

-continued

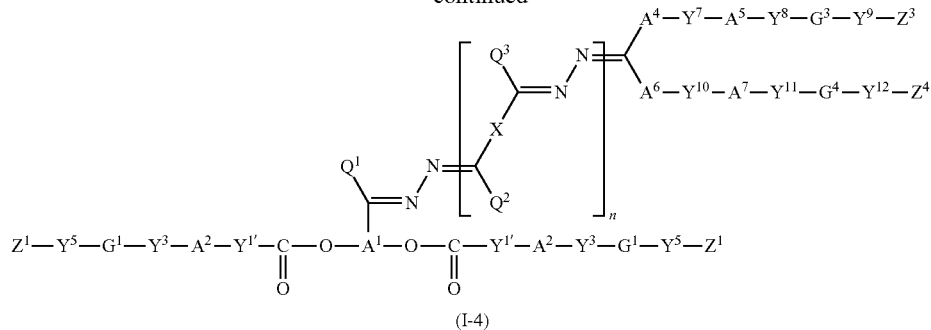

(I-4)

wherein $A^1$, $A^2$, $A^4$ to $A^7$, $Q^1$ to $Q^3$, $X$, $Y^{1'}$, $Y^3$, $Y^5$, $Y^7 \sim Y^{12}$, $G^1$, $G^3$, $G^4$, $Z^1$, $Z^3$, $Z^4$, n, and L are the same as defined above.

The compounds (4), (6), (10), and (12) used in the production method 1 or 2 may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

An ether linkage may be formed as described below, for example.

(i) A compound represented by D1-hal (wherein hal is a halogen atom; hereinafter the same) and a compound represented by D2-OMet (wherein Met is an alkali metal (mainly sodium; hereinafter the same)) are mixed and condensed (Williamson synthesis). Note that D1 and D2 are an arbitrary organic group (hereinafter the same).

(ii) A compound represented by D1-hal and a compound represented by D2-OH are mixed and condensed in the presence of a base (e.g., sodium hydroxide or potassium hydroxide).

(iii) A compound represented by D1-J (wherein J is an epoxy group) and a compound represented by D2-OH are mixed and condensed in the presence of a base (e.g., sodium hydroxide or potassium hydroxide).

(iv) A compound represented by D1-ofn (wherein ofn is a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below, for example.

(vi) A compound represented by D1-COOH and a compound represented by D2-OH or D2-NH₂ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or D2-NH₂ in the presence of a base.

(viii) A compound represented by D1-COOH is reacted with an acid anhydride to obtain a mixed acid anhydride, and the mixed acid anhydride is reacted with a compound represented by D2-OH or D2-NH₂.

(ix) A compound represented by D1-COOH and a compound represented by D2-OH or D2-NH₂ are subjected to dehydration and condensation in the presence of an acid catalyst or a base catalyst.

The carbonyl compound (1) used in the production method 1 may be produced by the following reaction using the compound (10) or the like, for example.

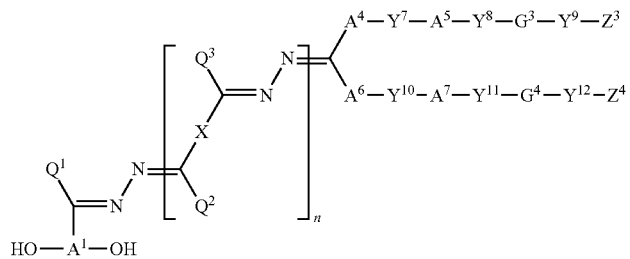

(9)

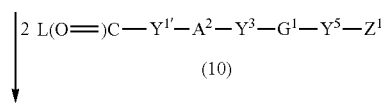

(10)

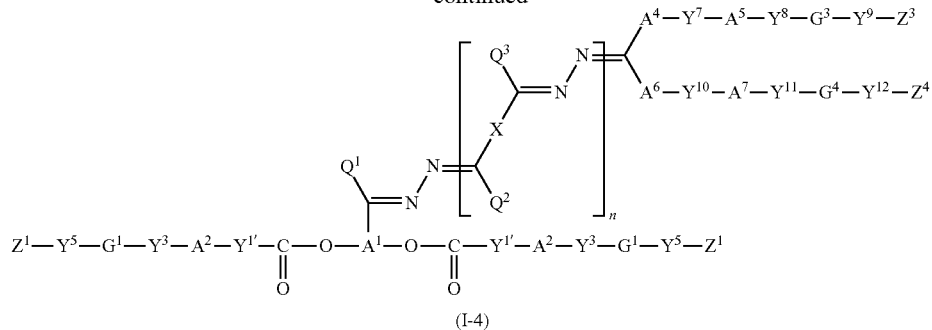

(I-4)

wherein $Y^{1'}$, $Y^3$, $Y^5$, $G^1$, $Z^1$, $A^1$, $A^2$, $Q^1$, and L are the same as defined above.

Specifically, the compound (1') wherein the group represented by $Z^2$—$Y^6$-$G^2$-$Y^4$-$A^3$-$Y^2$— is identical with the group represented by $Z^1$—$Y^5$-$G^1$-$Y^3$-$A^2$-$Y^1$—, and $Y^1$ is a group represented by $Y^{1'}$—C(=O)—O— can be obtained by reacting the compound (7) with a 2-fold equivalent of the compound (10). The above reaction may be effected in the same manner as the step 2 of the production method 1.

The compound (2) used in the production method 1 wherein n is 1 (compound (2')) may be produced as described below, for example.

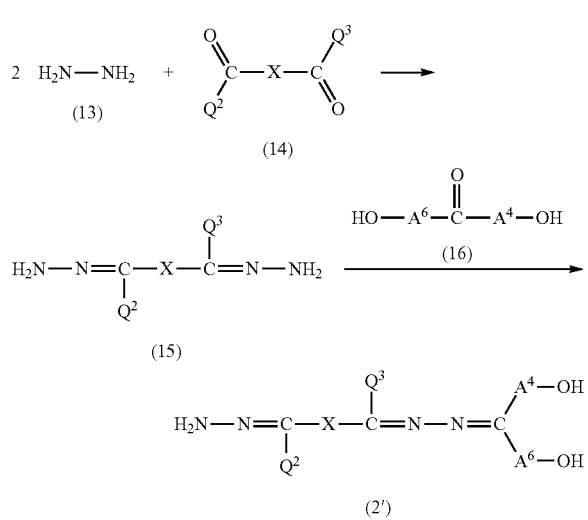

wherein $Q^2$, $Q^3$, $A^4$, $A^6$, and X are the same as defined above.

Specifically, the compound represented by the formula (14) (compound (14)) is reacted with a 2-fold equivalent or more of the hydrazine (13) in an appropriate solvent to obtain the compound (15), and the compound (15) is reacted with a 1-fold equivalent of the compound represented by the formula (16) (compound (16)) in an appropriate solvent to obtain the target compound (2').

Hydrazine monohydrate is normally used as the hydrazine (13). A commercially available product may be used directly as the hydrazine (13) (hereinafter the same).

The solvent used for the above reaction is not particularly limited as long as the solvent is inert to the reaction. Examples of the solvent include those mentioned above in connection with the step 1 of the production method 1.

The reaction proceeds smoothly when the reaction temperature is within the range from −10° C. to the boiling point of the solvent. The reaction time is determined taking account of the reaction scale, but is normally several minutes to several hours.

The compound (2) wherein n is 0 (compound (2")) may be produced by reacting the compound (16) with a 1-fold equivalent of the compound represented by the hydrazine (13) (see the following reaction formula).

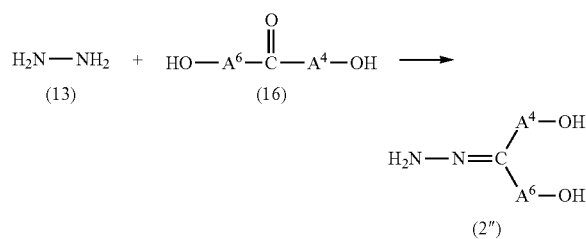

wherein $A^4$ and $A^6$ are the same as defined above.

The compound (8) used in the production method 2 may be produced by reacting the compound (2) with a 1-fold equivalent of the compound (4) in the same manner as in the step 2 of the production method 1, and reacting the reaction product with a 1-fold equivalent of the compound (6) in the same manner as in the step 3 of the production method 1, for example.

Production Method 3

The polymerizable compound represented by the formula (I-5) (polymerizable compound (I-5)) wherein the group represented by $Z^2$—$Y^6$-$G^2$-$Y^4$-$A^3$-$Y^{2'}$—, the group represented by $Z^3$—$Y^9$-$G^3$-$Y^8$-$A^5$-$Y^{7'}$—, and the group represented by $Z^4$—$Y^{12}$-$G^4$-$Y^{11}$-$A^7$-$Y^{10'}$— are identical with the group represented by $Z^1$—$Y^5$-$G^1$-$Y^3$-$A^2$-$Y^{1'}$— may be produced as described below (see the following reaction formula).

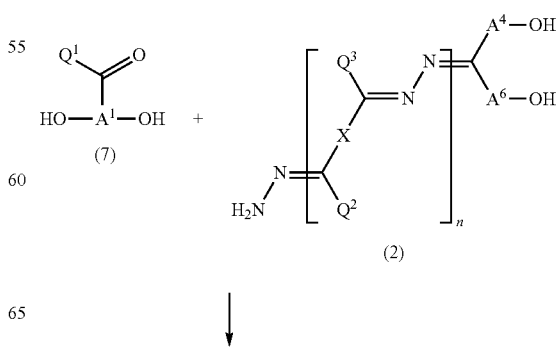

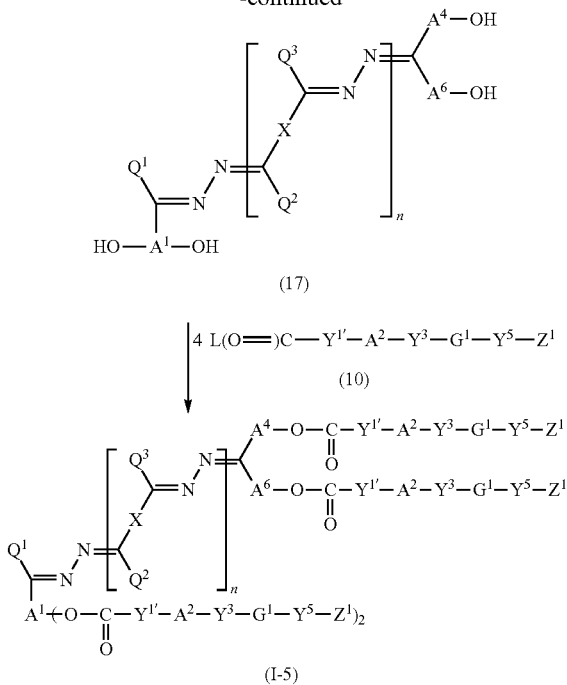

(17)

$$\downarrow 4\ L(O{=}){-}C{-}Y^{1'}{-}A^2{-}Y^3{-}G^1{-}Y^5{-}Z^1 \quad (10)$$

(I-5)

wherein $Y^{1'}, Y^3, Y^5, G^1, Z^1, A^1, A^2, A^4, A^6, Q^1$ to $Q^3$, n, X, and L are the same as defined above.

Specifically, the compound (2) used in the production method 1 is reacted with the compound (7) in the step 1 of the production method 2 instead of the compound (8) to obtain the compound represented by the formula (17), and the compound represented by the formula (17) is reacted with a 4-fold equivalent or more of the compound (10) in the same manner as in the step 2 of the production method 2 to obtain the target polymerizable compound (I-5).

The target product may be isolated by performing a post-treatment operation normally employed in organic chemistry after completion of the reaction, optionally followed by a known purification/separation means such as column chromatography, recrystallization, or distillation.

The structure of the target product may be identified by measurement (e.g., NMR spectrometry, IR spectrometry, or mass spectrometry), elemental analysis, or the like.

2) Polymerizable Composition

A polymerizable composition according to one embodiment of the invention includes the polymerizable compound according to one embodiment of the invention, and an initiator. The initiator is used to more efficiently polymerize the polymerizable composition according to one embodiment of the invention.

The initiator may be appropriately selected depending on the type of the polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group.

Examples of the radical initiator include a thermal radical generator that is a compound that generates active species that initiate polymerization of the polymerizable compound upon heating, and a photo-radical generator that is a compound that generates active species that initiate polymerization of the polymerizable compound upon exposure to exposure light (e.g., visible rays, ultraviolet rays (e.g., i-line), deep ultraviolet rays, electron beams, or X-rays). It is preferable to use the photo-radical generator.

Examples of the photo-radical generator include acetophenone-based compounds, biimidazole-based compounds, triazine-based compounds, O-acyloxime-based compounds, onium salt-based compounds, benzoin-based compounds, benzophenone-based compounds, α-diketone-based compounds, polynuclear quinone-based compounds, xanthone-based compounds, diazo-based compounds, imide sulfonate-based compounds, and the like. These compounds generate active radicals and/or an active acid upon exposure. These photo-radical generators may be used either alone or in combination.

Specific examples of the acetophenone-based compounds include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compounds include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compounds include triazine-based compounds that include a halomethyl group, such as
2,4,6-tris(trichloromethyl)-s-triazine, 2-methyl-4,6-bis(trichloromethyl)-s-triazine,
2-[2-(5-methylfuran-2-yl)ethenyl]-4,6-bis(trichloromethyl)-s-triazine,
2-[2-(furan-2-yl)ethenyl]-4,6-bis(trichloromethyl)-s-triazine,
2-[2-(4-diethylamino-2-methylphenyl)ethenyl]-4,6-bis(trichloromethyl)-s-triazine,
2-[2-(3,4-dimethoxyphenyl)ethenyl]-4,6-bis(trichloromethyl)-s-triazine,
2-(4-methoxyphenyl)-4,6-bis(trichloromethyl)-s-triazine, 2-(4-ethoxystyryl)-4,6-bis(trichloromethyl)-s-triazine, and
2-(4-n-butoxyphenyl)-4,6-bis(trichloromethyl)-s-triazine.

Specific examples of the O-acyloxime-based compounds include

1-[4-(phenylthio)phenyl]-heptane-1,2-dione-2-(O-benzoyloxime),
1-[4-(phenylthio)phenyl]-octane-1,2-dione-2-(O-benzoyloxime),
1-[4-(benzoyl)phenyl]-octane-1,2-dione-2-(O-benzoyloxime),
1-[9-ethyl-6-(2-methylbenzoyl)-9H-carbazol-3-yl]-ethanone-1-(O-acetyloxime),
1-[9-ethyl-6-(3-methylbenzoyl)-9H-carbazol-3-yl]-ethanone-1-(O-acetyloxime),
1-(9-ethyl-6-benzoyl-9H-carbazol-3-yl)-ethanone-1-(O-acetyloxime),
ethanone-1-[9-ethyl-6-(2-methyl-4-tetrahydrofuranylbenzoyl)-9H-carbazol-3-yl]-1-(O-acetyloxime),
ethanone-1-[9-ethyl-6-(2-methyl-4-tetrahydropyranylbenzoyl)-9H-carbazol-3-yl]-1-(O-acetyloxime),
ethanone-1-[9-ethyl-6-(2-methyl-5-tetrahydrofuranylbenzoyl)-9H-carbazol-3-yl]-1-(O-acetyloxime),
ethanone-1-[9-ethyl-6-(2-methyl-5-tetrahydropyranylbenzoyl)-9H-carbazol-3-yl]-1-(O-acetyloxime),
ethanone-1-[9-ethyl-6-{2-methyl-4-(2,2-dimethyl-1,3-dioxolanyl)benzoyl}-9H-carbazol-3-yl]-1-(O-acetyloxime),
ethanone-1-[9-ethyl-6-(2-methyl-4-tetrahydrofuranylmethoxybenzoyl)-9H-carbazol-3-yl]-1-(O-acetyloxime),
ethanone-1-[9-ethyl-6-(2-methyl-4-tetrahydropyranylmethoxybenzoyl)-91'-carbazol-3-yl]-1-(O-acetyloxime),
ethanone-1-[9-ethyl-6-(2-methyl-5-tetrahydrofuranylmethoxybenzoyl)-9H-carbazol-3-yl]-1-(O-acetyloxime),
ethanone-1-[9-ethyl-6-(2-methylbenzoyl)-9H-carbazol-3-yl]-1-(O-acetyloxime),
ethanone-1-[9-ethyl-6-(2-methyl-5-tetrahydropyranylmethoxybenzoyl)-9H-carbazol-3-yl]-1-(O-acetyloxime),
ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available photo-radical generator may be used directly. Specific examples of a commercially available photo-radical generator include Irgacure 907, Irgacure 184, Irgacure 369, Irgacure 651, Irgacure 819, Irgacure 907, Irgacure OXE02 (manufactured by BASF); Adekaoptomer N1919 (manufactured by Adeka Corporation); and the like.

Examples of the anionic initiator include alkyllithium compounds; monolithium salts or monosodium salts of biphenyl, naphthalene, pyrene, and the like; polyfunctional initiators such as dilithiums and trilithium salts; and the like.

Examples of the cationic initiator include proton acids such as sulfuric acid, phosphoric acid, perchloric acid, and trifluoromethanesulfonic acid; Lewis acids such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally added to the polymerizable composition according to one embodiment of the invention in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust surface tension. The surfactant is not particularly limited, but is preferably a nonionic surfactant. Examples of the nonionic surfactant include an oligomer having a molecular weight of about several thousand, such as KH-40 (manufactured by AGC Seimi Chemical Co., Ltd.). The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide). Each additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate solvent.

Examples of the solvent include ketones such as cyclopentanone, cyclohexanone, and methyl ethyl ketone; acetates such as butyl acetate and amyl acetate; halogenated hydrocarbons such as chloroform, dichloromethane, and dichloroethane; ethers such as 1,4-dioxane, cyclopentyl methyl ether, tetrahydrofuran, tetrahydropyran, and 1,3-dioxolane; and the like.

The polymerizable composition thus obtained is useful as a raw material for producing a polymer or an optically anisotropic article according to the embodiments of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amyltolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like. Examples of a commercially available product of the additional copolymerizable monomer include LC-242 (manufactured by BASF).

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include alkanediol diacrylates such as 1,2-butanediol diacrylate, 1,3-butanediol diacrylate, 1,4-butanediol diacrylate, neopentanediol diacrylate, and 1,6-hexanediol diacrylate, alkanediol dimethacrylates such as 1,2-butanediol dimethacrylate, 1,3-butanediol dimethacrylate, 1,4-butanediol dimethacrylate, neopentanediol dimethacrylate, and 1,6-hexanediol dimethacrylate, polyethylene glycol diacrylates such as ethylene glycol diacrylate, diethylene glycol diacrylate, triethylene glycol diacrylate, and tetraethylene glycol diacrylate, polypropylene glycol diacrylates such as propylene glycol diacrylate, dipropylene glycol diacrylate, tripropylene glycol diacrylate, and tetrapropylene glycol diacrylate, polyethylene glycol dimethacrylates such as ethylene glycol dimethacrylate, diethylene glycol dimethacrylate, triethylene glycol dimethacrylate, and tetraethylene glycol dimethacrylate, polypropylene glycol dimethacrylates such as propylene glycol dimethacrylate, dipropylene glycol dimethacrylate, tripropylene glycol dimethacrylate, and tetrapropylene glycol dimethacrylate, polyethylene glycol divinyl ethers such as ethylene glycol divinyl ether, diethylene glycol divinyl ether, triethylene glycol divinyl ether, and tetraethylene glycol divinyl ether, polyethylene glycol diallyl ethers such as ethylene glycol diallyl ether, diethylene glycol diallyl ether, triethylene glycol diallyl ether, and tetraethylene glycol diallyl ether, bisphenol F ethoxylate diacrylate, bisphenol F ethoxylate dimethacrylate, bisphenol A ethoxylate diacrylate, bisphenol A ethoxylate dimethacrylate, trimethylolpropane triacrylate, trimethylolpropane trimethacrylate, trimethylolpropane ethoxylate triacrylate, trimethylolpropane ethoxylate trimethacrylate, trimethylolpropane propoxylate triacrylate, trimethylolpropane propoxylate trimethacrylate, isocyanuric acid ethoxylate triacrylate, glycerol ethoxylate triacrylate, glycerol propoxylate triacrylate, pentaerythritol ethoxylate tetraacrylate, ditrimethylolpropane ethoxylate tetraacrylate, dipentaerythritol ethoxylate hexacrylate, and the like.

The polymerizable compound according to one embodiment of the invention may be (co)polymerized together with an optional additional copolymerizable monomer optionally in the presence of an appropriate initiator. The initiator may be used in an amount similar to that of the initiator included in the polymerizable composition.

When the polymer according to one embodiment of the invention is a copolymer of the polymerizable compound according to one embodiment of the invention and the additional copolymerizable monomer, the content of constituent units derived from the polymerizable compound according to one embodiment of the invention is not particularly limited, but is preferably 50 wt % or more, and more preferably 70 wt % or more, based on the amount of the total constituent units. When the content of constituent units derived from the polymerizable compound is within the above range, a polymer that has a high glass transition temperature (Tg) and high hardness can be obtained.

The polymer (1) may be produced by (A) (co)polymerizing the polymerizable compound together with an optional additional copolymerizable monomer in an appropriate organic solvent optionally in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound in an organic solvent together with an optional additional copolymerizable monomer and an optional initiator to a substrate using a known coating method, removing the solvent, and effecting polymerization by applying heat or activated energy rays, for example.

Examples of the initiator include those mentioned above in connection with the initiator included in the polymerizable composition.

The organic solvent used for the method (A) is not particularly limited as long as the organic solvent is inert. Examples of the organic solvent used for the polymerization reaction when using the method (A) include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; ethers such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

Examples of the organic solvent used to dissolve the polymer when using the method (A) include ketone-based solvents such as acetone, methyl ethyl ketone, methyl isobutyl ketone, cyclopentanone, and cyclohexanone; ester-based solvents such as butyl acetate and amyl acetate; halogenated hydrocarbon-based solvents such as dichloromethane, chloroform, and dichloroethane; ether-based solvents such as tetrahydrofuran, tetrahydropyran, 1,2-dimethoxyethane, 1,4-dioxane, cyclopentyl methyl ether, and 1,3-dioxolane; and the like.

Examples of the organic solvent used in the method (B) include ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; ethers such as tetrahydrofuran, tetrahydropyran, 1,2-dimethoxyethane, 1,4-dioxane, cyclopentyl methyl ether, and 1,3-dioxolane; and the like. Among these, it is preferable to use a compound having a boiling point of 60 to 200° C. from the viewpoint of handling capability.

A substrate formed of a known organic or inorganic material may be used as the substrate. Examples of the organic material include polycycloolefins (e.g., Zeonex, Zeonor (registered trademark; manufactured by Zeon Corporation), Arton (registered trademark; manufactured by JSR Corporation), and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate formed of an organic material, and more preferably a resin film formed of the organic material.

The polymer solution (method (A)) or the solution that is subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the above initiator (particularly a photoinitiator) in order to ensure efficient polymerization.

It is preferable to produce the polymer according to one embodiment of the invention by applying the polymerizable composition according to one embodiment of the invention to a substrate, and polymerizing the applied polymerizable composition (i.e., method (B)). Examples of the substrate include a substrate used to produce an optically anisotropic article (described later).

The polymerizable composition according to one embodiment of the invention may be applied to the substrate by a known coating method (e.g., bar coating method, spin coating method, roll coating method, gravure coating method, spray coating method, die coating method, cap coating method, or dipping method). A known organic solvent may be added to the polymerizable composition in order to improve the applicability of the polymerizable composition. In this case, it is preferable to remove the organic solvent by natural drying, drying by heating, drying under reduced pressure, drying by heating under reduced pressure, or the like after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition from the viewpoint of convenience.

The temperature during application is preferably 30° C. or less. The UV dose is normally 1 $W/m^2$ to 10 $kW/m^2$, and preferably 5 $W/m^2$ to 2 $kW/m^2$.

A polymer obtained by polymerizing the polymerizable compound according to one embodiment of the invention or the polymerizable composition according to one embodiment of the invention may be independently used after removing the polymer from the substrate, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluant: tetrahydrofuran).

It is considered that the polymer according to one embodiment of the invention has a structure in which crosslinking points are uniformly present in the molecule, and exhibits a high crosslinking efficiency and excellent hardness.

The polymer according to one embodiment of the invention makes it possible to inexpensively obtain an optical film that achieves uniform conversion of polarized light over a wide wavelength band.

4) Optically Anisotropic Article

An optically anisotropic article according to one embodiment of the invention includes the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film includes a polymer such as a polyimide, polyvinyl alcohol, polyester, polyallylate, polyamideimide, or polyetherimide. The alignment film may be obtained by applying a solution (alignment film-forming composition) that includes such a polymer to the substrate to form a film, drying the film, and performing a rubbing treatment in one direction, for example.

The thickness of the alignment film is preferably 0.001 to 5 µm, and more preferably 0.001 to 1 µm.

The rubbing treatment may be performed on the alignment film or the substrate. The rubbing treatment may be implemented by an arbitrary method. For example, the alignment film may be rubbed in a given direction using a roll around which a cloth or felt formed of synthetic fibers (e.g., nylon) or natural fibers (e.g., cotton) is wound. It is preferable to wash the alignment film with isopropyl alcohol or the like after the rubbing treatment in order to remove fine powder (foreign substances) formed during the rubbing treatment to clean the surface of the alignment film.

The alignment film may be provided with a function of achieving in-plane alignment of a cholesteric liquid crystal layer by applying polarized UV rays to the surface of the alignment film.

The liquid crystal layer may be formed on the alignment film using the polymer according to one embodiment of the invention using the method described above in connection with the polymer according to one embodiment of the invention.

Since the optically anisotropic article according to one embodiment of the invention is produced using the polymer according to one embodiment of the invention, the optically anisotropic article can be produced at low cost, achieves uniform conversion of polarized light over a wide wavelength band, and shows satisfactory performance.

Examples of the optically anisotropic article according to one embodiment of the invention include a retardation film, an alignment film for liquid crystal display elements (liquid crystal displays), a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

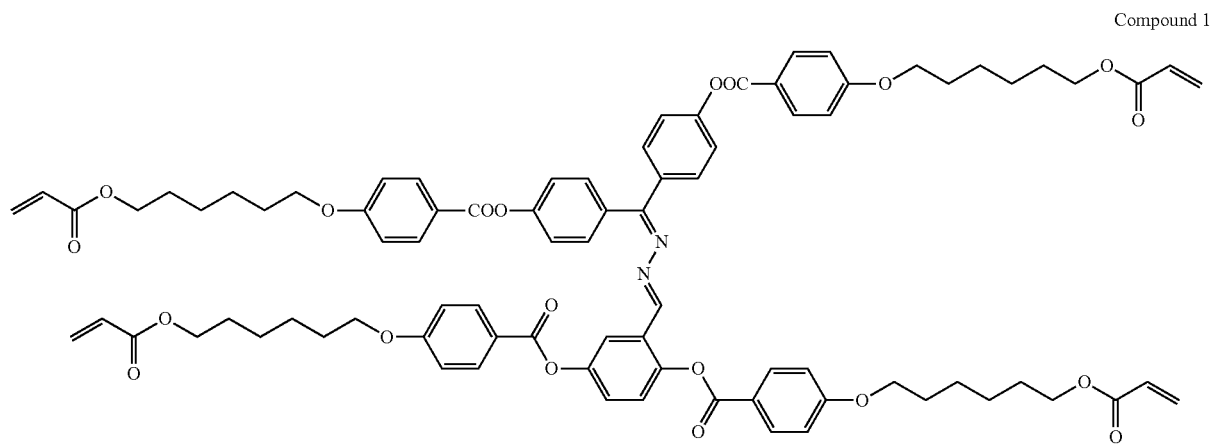

Compound 1

Step 1: Synthesis of Intermediate A

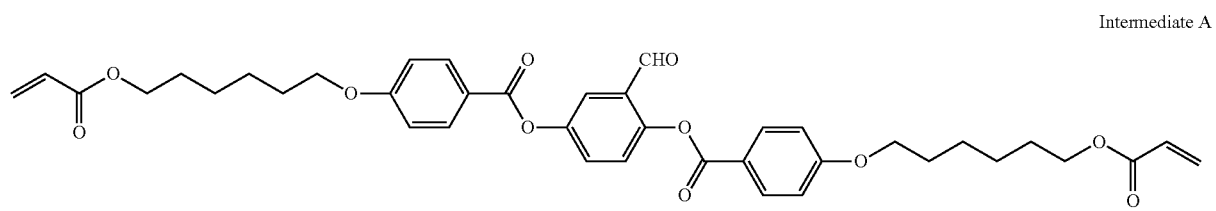 [SMILES: C=CC(=O)OCCCCCCOc1ccc(C(=O)Oc2ccc(OC(=O)c3ccc(OCCCCCCOC(=O)C=C)cc3)c(C=O)c2)cc1]

Intermediate A

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a homogeneous solution. After the addition of 83.3 g (434.4 mmol) of 1-ethyl-3-(3-dimethylaminopropyl)carbodiimide hydrochloride (WSC) to the solution, the mixture was stirred at 25° C. for 12 hours.

After completion of the reaction, the reaction mixture was added to 1.5 l of water, and extracted with 500 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 75 g of an intermediate A as a white solid (yield: 75.4%). The structure of the target product was identified by $^1$H-NMR.

$^1$H-NMR Data for Intermediate A $^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H).

Step 2: Synthesis of Intermediate B

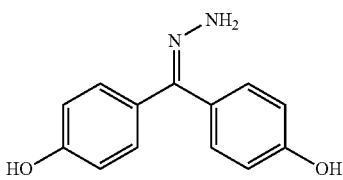

Intermediate B

A three-necked reactor equipped with a thermometer was charged with 3.51 g (70.0 mol) of hydrazine monohydrate, 15 ml of 1-propanol, and 1.5 g (7.00 mol) of 4,4'-dihydroxybenzophenone under a nitrogen stream, and the mixture was refluxed for 7 hours.

After completion of the reaction, the reaction mixture was cooled to 25° C., added to 100 ml of saturated sodium bicarbonate water, and extracted three times with 50 ml of chloroform. The chloroform layer was collected, washed with 50 ml of a saturated sodium chloride solution, and dried over anhydrous sodium sulfate, and sodium sulfate was filtered off. Chloroform was evaporated from the filtrate under reduced pressure using a rotary evaporator to obtain 1.6 g of an intermediate B as a white solid. The solid was then dried, and used directly for the subsequent reaction without purification.

The structure of the target product was identified by $^1$H-NMR.

¹H-NMR Data for Intermediate B

¹H-NMR (400 MHz, DMSO-d₆, TMS, δ ppm): 9.64 (s, 1H), 9.39 (s, 1H), 7.12 (d, 2H, J=8.7 Hz), 7.06 (d, 2H, J=8.7 Hz), 6.96 (d, 2H, J=8.7 Hz), 6.86 (d, 2H, J=8.7 Hz), 5.82 (s, 2H).

Step 3: Synthesis of Intermediate C

Step 4: Synthesis of Compound 1

A four-necked reactor equipped with a thermometer was charged with 1.0 g (1.11 mmol) of the intermediate C synthesized in the step 3, 0.8 g (2.74 mmol) of 4-(6-acryloylhex-1-yloxy)benzoic acid (manufactured by DKSH Japan K.K.), 0.34 mg (2.74 mmol) of 4-(dimethylamino)pyridine, and 20

Intermediate C

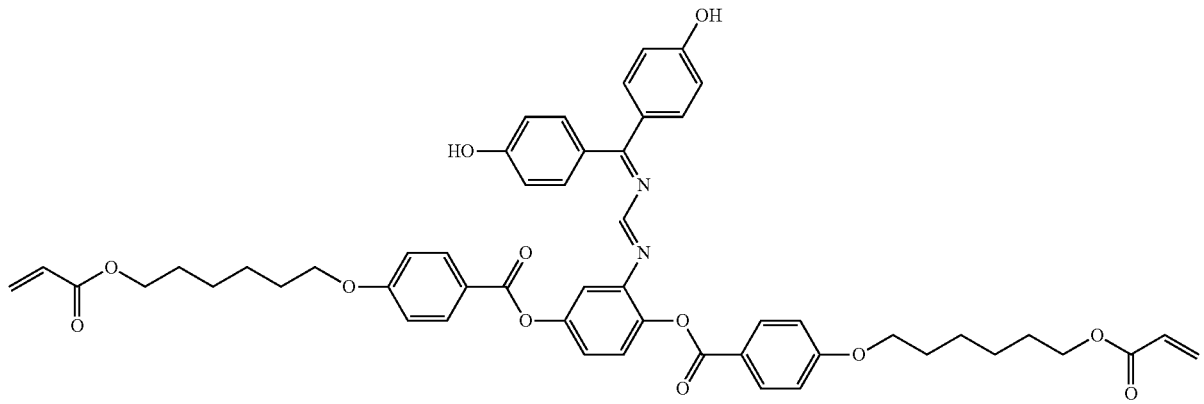

A four-necked reactor equipped with a thermometer was charged with 2.4 g (3.49 mmol) of the intermediate A synthesized in the step 1 and 20 ml of tetrahydrofuran (THF) under a nitrogen stream to prepare a homogeneous solution. 1.0 g (4.38 mmol) of the intermediate B synthesized in the step 2 was added to the solution. A solution prepared by dissolving 10 mg (0.43 mmol) of (±)-10-camphorsulfonic acid in 3 ml of THF was slowly added to the solution. The mixture was then stirred at 25° C. for 2 hours.

After completion of the reaction, the reaction mixture was added to 200 ml of saturated sodium bicarbonate water, and extracted twice with 50 ml of ethyl acetate. The ethyl acetate layer was collected, washed with 100 ml of a saturated sodium chloride solution, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=70:30 (volume ratio)) to obtain 1.9 g of an intermediate C as a yellow solid (yield: 60.7%).

The structure of the target product was identified by ¹H-NMR.

¹H-NMR Data for Intermediate C

¹H-NMR (500 MHz, CDCl₃, TMS, δ ppm): 8.70 (s, 1H), 8.113 (d, 2H, J=8.5 Hz), 8.090 (d, 2H, J=8.5 Hz), 7.74 (d, 1H, J=3.0 Hz), 7.48 (d, 2H, J=8.5 Hz), 7.30 (dd, 1H, J=2.5 Hz, 8.5 Hz), 7.27 (d, 1H, J=8.5 Hz), 7.15 (d, 2H, J=8.5 Hz), 6.94 (d, 4H, J=8.5 Hz), 6.75-6.72 (m, 4H), 6.412 (dd, 1H, J=1.5 Hz, 17.5 Hz), 6.409 (dd, 1H, J=1.5 Hz, 17.5 Hz), 6.128 (dd, 1H, J=10.5 Hz, 17.5 Hz), 6.126 (dd, 1H, J=10.5 Hz, 17.5 Hz), 5.833 (dd, 1H, J=1.5 Hz, 10.5 Hz), 5.830 (dd, 1H, J=1.5 Hz, 10.5 Hz), 4.18 (t, 4H, J=6.5 Hz), 4.034 (t, 2H, J=6.5 Hz), 4.030 (t, 2H, J=6.5 Hz), 1.85-1.79 (m, 4H), 1.75-1.69 (m, 4H), 1.55-1.42 (m, 8H).

ml of N-methylpyrrolidone under a nitrogen stream to prepare a homogeneous solution. After the addition of 0.63 g (3.29 mmol) of WSC to the solution, the mixture was stirred at 25° C. for 14 hours.

After completion of the reaction, the reaction mixture was added to 200 ml of water, and extracted with 100 ml of ethyl acetate. The ethyl acetate layer was dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.0 g of a compound 1 as a light yellow solid (yield: 62.3%).

The structure of the target product was identified by ¹H-NMR.

¹H-NMR Data for Compound 1

¹H-NMR (500 MHz, CDCl₃, TMS, δ ppm): 8.70 (s, 1H), 8.17-8.10 (m, 8H), 7.76-7.73 (m, 3H), 7.41-7.38 (m, 2H), 7.34 (dd, 1H, J=3.0 Hz, 9.0 Hz), 7.29-7.27 (m, 3H), 7.23 (d, 2H, J=9.0 Hz), 6.99-6.93 (m, 8H), 6.410 (dd, 2H, J=1.5 Hz, 17.5 Hz), 6.407 (dd, 2H, J=17.5 Hz), 6.131 (dd, 2H, J=10.5 Hz, 17.5 Hz), 6.127 (dd, 2H, J=10.5 Hz, 17.5 Hz), 5.828 (dd, 2H, J=1.5 Hz, 10.5 Hz), 5.822 (dd, 2H, J=1.5 Hz, 10.5 Hz), 4.20-4.17 (m, 8H), 4.07-4.02 (m, 8H), 1.89-1.82 (m, 8H), 1.76-1.70 (m, 8H), 1.58-1.43 (m, 16H).

Measurement of Phase Transition Temperature

The phase transition temperature was measured by the following method using the compound 1 obtained in Example 1, the compound 1r (i.e., the compound disclosed in JP-A-2008-291218) of Reference Example 1 that was used in Comparative Example 1, and the compound 2r ("LC242" manufactured by BASF) of Reference Example 2 that was used in Comparative Example 2.

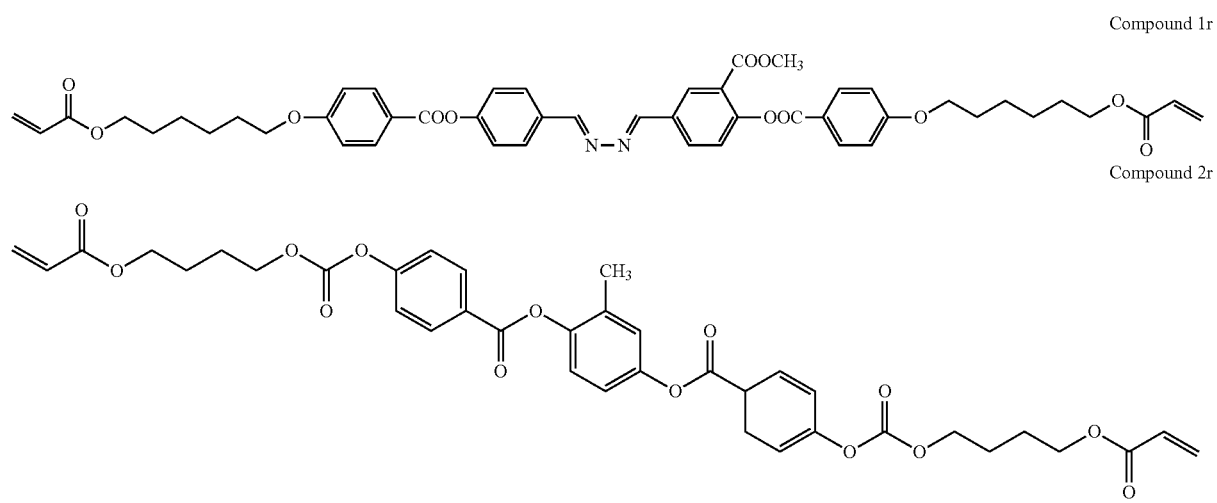

Specifically, 10 mg of each compound (compound 1, compound 1r of Reference Example 1, and compound 2r of Reference Example 2) was weighed, and placed in a solid state between two glass substrates provided with a polyimide alignment film subjected to a rubbing treatment (manufactured by E.H.C. Co. Ltd.). The substrates were placed on a hot plate, heated from 50° C. to 200° C., and cooled to 50° C. A change in structure when the temperature was changed was observed using a polarizing microscope ("ECLIPSE LV100 POL" manufactured by Nikon Corporation).

The phase transition temperature measurement results are shown in Table 1.

In Table 1, "C" refers to "crystal", "N" refers to "nematic", and "I" refers to "isotropic". The term "crystal" means that the test compound was in a solid phase, the term "nematic" means that the test compound was in a nematic liquid crystal phase, and the term "isotropic" means that the test compound was in an isotropic liquid phase.

TABLE 1

| Polymerizable compound | | Phase transition temperature | | |
|---|---|---|---|---|
| Example 1 | Compound 1 | C ⇌ (85° C. / 50° C. or less) N ⇌ (109° C. / 102° C.) I |
| Reference Example 1 | Compound 1r | C ⇌ (80° C. / 50° C. or less) N ⇌ (200° C. or more) I |
| Reference Example 2 | Compound 2r | C ⇌ (60° C. / 50° C. or less) N ⇌ (123° C. / 122° C.) I |

Example 2 and Comparative Examples 1 and 2

1 g of each compound (compound 1 obtained in Example 1, compound 1r of Reference Example 1, and compound 2r of Reference Example 2), 30 mg of a photoinitiator ("Adekaoptomer N-1919" manufactured by Adeka Corporation), and 100 mg of a 1% cyclopentanone solution of a surfactant ("KH-40" manufactured by AGC Seimi Chemical Co., Ltd.) were dissolved in 2.3 g of cyclopentanone. The solution was filtered through a disposable filter having a pore size of 0.45 μm to obtain a polymerizable composition (polymerizable compositions 1, 1r, and 2r).

The polymerizable compositions 1, 1r, and 2r were polymerized by the following method to obtain polymers. The retardation was measured, and the wavelength dispersion was evaluated using the resulting polymers.

Measurement of Retardation and Evaluation of Wavelength Dispersion (i) Preparation of Transparent Resin Substrate Provided with Alignment Film Each side of an alicyclic olefin polymer film ("ZeonorFilm ZF16-100" manufactured by Zeon Corporation) (thickness: 100 μm) was subjected to a corona discharge treatment. A 5% polyvinyl alcohol aqueous solution was applied to one side of the film using a #2 wire bar, and the film was dried to form an alignment film having a thickness of 0.1 μm. The alignment film was subjected to a rubbing treatment to prepare a transparent resin substrate on which the alignment film was formed.

(ii) Formation of Liquid Crystal Layer

Each polymerizable composition (polymerizable compositions 1, 1r, and 2r) was applied to the surface of the transparent resin substrate on which the alignment film was formed, using a #4 wire bar. After drying the film for 30 seconds at the temperature (drying temperature) shown in Table 2, the film was subjected to an alignment treatment for 1 minute at the temperature (alignment treatment temperature) shown in Table 2 to form a liquid crystal layer having a thickness of about 1.5 μM. UV rays were applied to the liquid crystal layer at a dose of 2000 mJ/cm$^2$ to effect polymerization to prepare a wavelength dispersion measurement sample.

(iii) Measurement of Retardation

The retardation between 400 nm and 800 nm was measured using the sample utilizing an ellipsometer ("XLS-100" manufactured by J. A. Woollam).

(iv) Evaluation of Wavelength Dispersion

The wavelength dispersion was evaluated from the values α and β calculated by the following expressions using the measured retardation.

The value α is smaller than 1, and the value β is larger than 1 when reverse wavelength dispersion is achieved, and the values α and β are almost identical when flat wavelength dispersion is achieved.

α=(retardation at 450 nm)/(retardation at 550 nm)

β=(retardation at 650 nm)/(retardation at 550 nm)

TABLE 2

| | Polymerizable compound | Drying temperature (° C.) | Alignment treatment temperature (° C.) | α Re (450)/ Re(550) | β Re (650)/ Re(550) |
|---|---|---|---|---|---|
| Example 2 | Compound 1 | 95 | 23 | 1.031 | 0.999 |
| Comparative Example 1 | Compound 1r | 90 | 23 | 1.193 | 0.918 |
| Comparative Example 2 | Compound 2r | 80 | 23 | 1.086 | 0.970 |

As shown in Table 2, the values α and β were almost identical (i.e., flat wavelength dispersion was achieved) when using the polymer obtained in Example 1.

When using the polymers obtained in Comparative Examples 1 and 2, the value α was significantly larger than 1, and the difference between the value α and the value β was large.

The invention claimed is:

1. A polymerizable compound represented by a general formula (I), $$Z^1-Y^5-G^1-Y^3-A^2-Y^1-A^1-Y^2-A^3-Y^4-G^2-Y^6-Z^2$$
$$A^4-Y^7-A^5-Y^8-G^3-Y^9-Z^3$$
$$A^6-Y^{10}-A^7-Y^{11}-G^4-Y^{12}-Z^4$$

wherein $Q^1$ to $Q^3$ are independently a hydrogen atom, or a substituted or unsubstituted alkyl group having 1 to 6 carbon atoms, X is a substituted or unsubstituted divalent aromatic group having 4 to 12 carbon atoms, $Y^1$ to $Y^{12}$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, $G^1$ to $G^4$ are independently a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)— (excluding a case where the aliphatic group includes two or more adjacent —O— or —S—), $R^2$ is a hydrogen atom or an alkyl group having 1 to 6 carbon atoms, $Z^1$ to $Z^4$ are independently an alkenyl group having 2 to 10 carbon atoms that is substituted with a halogen atom, or unsubstituted, $A^1$ is a substituted or unsubstituted trivalent aromatic group, $A^2$ to $A^7$ are independently a substituted or unsubstituted divalent aromatic group having 4 to 30 carbon atoms, and n is 0 or 1.

2. The polymerizable compound according to claim 1, wherein $A^1$ in the general formula (I) is a substituted or unsubstituted trivalent benzene ring group, or a substituted or unsubstituted trivalent naphthalene ring group, and $A^2$ to $A^7$ in the general formula (I) are independently a substituted or unsubstituted phenylene group, or a substituted or unsubstituted naphthylene group.

3. The polymerizable compound according to claim 1, wherein $Y^1$ to $Y^{12}$ in the general formula (I) are independently a chemical single bond, —O—, —O—C(=O)—, —C(=O)—O—, or —O—C(=O)—O—.

4. The polymerizable compound according to claim 1, wherein $Z^1$ to $Z^4$ in the general formula (I) are independently CH$_2$=CH—, CH$_2$=C(CH$_3$)—, or CH$_2$=C(Cl)—.

5. The polymerizable compound according to claim 1, wherein $G^1$ to $G^4$ in the general formula (I) are independently a substituted or unsubstituted divalent aliphatic group having 1 to 12 carbon atoms that optionally includes —O—, —O—C(=O)—, —C(=O)—O—, or —C(=O)— (excluding a case where the aliphatic group includes two or more adjacent —O—).

6. The polymerizable compound according to claim 1, wherein X in the general formula (I) is a substituted or unsubstituted phenylene group, a substituted or unsubstituted naphthylene group, or a substituted or unsubstituted biphenylene group.

7. The polymerizable compound according to claim 1, wherein $A^1$ in the general formula (I) is a substituted or unsubstituted trivalent benzene ring group, $A^2$ to $A^7$ in the general formula (I) are independently a substituted or unsubstituted phenylene group, $Y^1$ to $Y^{12}$ in the general formula (I) are independently a chemical single bond, —O—, —O—C(=O)—, —C(=O)—O—, or —O—C(=O)—O—, $Z^1$ to $Z^4$ in the general formula (I) are independently CH$_2$=CH—, CH$_2$=C(CH$_3$)—, or CH$_2$=C(Cl)—, and $G^1$ to $G^4$ in the general formula (I) are independently a divalent alkylene group having 1 to 12 carbon atoms.

8. A polymerizable composition comprising at least one of the polymerizable compound according to claim 1, and an initiator.

9. A polymer obtained by polymerizing the polymerizable compound according to claim 1.

10. An optically anisotropic article comprising the polymer according to claim 9.

11. The polymerizable compound according to claim 2, wherein $Y^1$ to $Y^{12}$ in the general formula (I) are independently a chemical single bond, —O—, —O—C(=O)—, —C(=O)—O—, or —O—C(=O)—O—.

12. The polymerizable compound according to claim 2, wherein $Z^1$ to $Z^4$ in the general formula (I) are independently CH$_2$=CH—, CH$_2$=C(CH$_3$)—, or CH$_2$=C(Cl)—.

13. The polymerizable compound according to claim 3, wherein $Z^1$ to $Z^4$ in the general formula (I) are independently CH$_2$=CH—, CH$_2$=C(CH$_3$)—, or CH$_2$=C(Cl)—.

14. The polymerizable compound according to claim 2, wherein $G^1$ to $G^4$ in the general formula (I) are independently a substituted or unsubstituted divalent aliphatic group having 1 to 12 carbon atoms that optionally includes —O—, —O—C(=O)—, —C(=O)—O—, or —C(=O)— (excluding a case where the aliphatic group includes two or more adjacent —O—).

15. The polymerizable compound according to claim 3, wherein $G^1$ to $G^4$ in the general formula (I) are independently a substituted or unsubstituted divalent aliphatic group having 1 to 12 carbon atoms that optionally includes —O—, —O—C(=O)—, —C(=O)—O—, or —C(=O)— (excluding a case where the aliphatic group includes two or more adjacent —O—).

16. The polymerizable compound according to claim 4, wherein $G^1$ to $G^4$ in the general formula (I) are independently a substituted or unsubstituted divalent aliphatic group having 1 to 12 carbon atoms that optionally includes —O—, —O—C(=O)—, —C(=O)—O—, or —C(=O)— (excluding a case where the aliphatic group includes two or more adjacent —O—).

17. The polymerizable compound according to claim 2, wherein X in the general formula (I) is a substituted or unsubstituted phenylene group, a substituted or unsubstituted naphthylene group, or a substituted or unsubstituted biphenylene group.

18. The polymerizable compound according to claim 3, wherein X in the general formula (I) is a substituted or unsubstituted phenylene group, a substituted or unsubstituted naphthylene group, or a substituted or unsubstituted biphenylene group.

19. The polymerizable compound according to claim 4, wherein X in the general formula (I) is a substituted or unsubstituted phenylene group, a substituted or unsubstituted naphthylene group, or a substituted or unsubstituted biphenylene group.

20. The polymerizable compound according to claim 5, wherein X in the general formula (I) is a substituted or unsubstituted phenylene group, a substituted or unsubstituted naphthylene group, or a substituted or unsubstituted biphenylene group.

* * * * *